(12) United States Patent
Nakagaki et al.

(10) Patent No.: US 7,156,966 B2
(45) Date of Patent: Jan. 2, 2007

(54) NOX-DECOMPOSING ELECTRODE AND NOX CONCENTRATION-MEASURING APPARATUS

(75) Inventors: Kunihiko Nakagaki, Nagoya (JP); Hideyuki Suzuki, Kasugai (JP); Sang Jae Lee, Ama-Gun (JP); Osamu Nakasone, Inabe-Gun (JP)

(73) Assignee: NGK Insulators, Ltd., Nagoya (JP)

( * ) Notice: Subject to any disclaimer, the term of this patent is extended or adjusted under 35 U.S.C. 154(b) by 676 days.

(21) Appl. No.: 10/419,391

(22) Filed: Apr. 21, 2003

(65) Prior Publication Data

US 2003/0201171 A1   Oct. 30, 2003

(30) Foreign Application Priority Data

Apr. 26, 2002   (JP) .............................. 2002-127383

(51) Int. Cl.
*G01N 27/30* (2006.01)
*G01N 27/407* (2006.01)

(52) U.S. Cl. ................. 204/426; 204/290.14; 205/781; 73/23.31

(58) Field of Classification Search ........... 204/290.08, 204/290.14, 424, 426, 429; 205/781, 784, 205/784.5; 73/23.31
See application file for complete search history.

(56) References Cited

U.S. PATENT DOCUMENTS

| | | | |
|---|---|---|---|
| 4,863,583 A | 9/1989 | Kurachi et al. | |
| 6,274,016 B1 | 8/2001 | Hasei et al. | |
| 6,280,588 B1 | 8/2001 | Kato et al. | |
| 6,419,818 B1 | 7/2002 | Kato et al. | |
| 6,673,223 B1 * | 1/2004 | Kunimoto et al. | 204/426 |

FOREIGN PATENT DOCUMENTS

| | | |
|---|---|---|
| EP | 0 859 233 A2 | 8/1998 |
| EP | 0 971 228 A2 | 1/2000 |
| EP | 1006352 | 6/2000 |
| EP | 1 211 508 A2 | 6/2002 |
| EP | 0 971 228 A3 | 1/2004 |
| JP | 63-266352 | 11/1988 |
| JP | 10-227760 | 8/1998 |
| JP | 11-183434 | 7/1999 |
| JP | 2000-28576 | 1/2000 |
| JP | 2000-171436 | 6/2000 |

OTHER PUBLICATIONS

Practical Handbook of Material Science, 1989, CRC Press, tables 6.2-5 and 6.2-6.*
Pt-Rh density from Platinum Metals Review, date unknown.*
U.S. Appl. No. 10/419,392, filed Apr. 2003, Nakagaki et al.

* cited by examiner

*Primary Examiner*—Kaj K. Olsen
(74) *Attorney, Agent, or Firm*—Burr & Brown

(57) ABSTRACT

A detecting electrode comprises a first cermet electrode layer formed directly on a solid electrolyte layer and a second cermet electrode layer formed on the first cermet electrode layer. A ratio between an alloy of Pt—Rh and $ZrO_2$ in the first cermet electrode layer ranges from 20:80 to 50:50 by volume ratio. On the other hand, a ratio between an alloy of Pt—Rh and $ZrO_2$ in the second cermet electrode layer ranges from 60:40 to 50:50 by volume ratio.

3 Claims, 7 Drawing Sheets

FIG. 3

| NOx CONCENTRATION-MEASURING APPARATUS | ALLOY (% BY VOLUME) | $ZrO_2$ (% BY VOLUME) |
|---|---|---|
| EXAMPLE 1 | 50 | 50 |
| EXAMPLE 2 | 40 | 60 |
| EXAMPLE 3 | 30 | 70 |
| EXAMPLE 4 | 20 | 80 |
| COMPARATIVE EXAMPLE 1 | 60 | 40 |

FIG. 5

| NOx CONCENTRATION-MEASURING APPARATUS | Rh (wt%) | Pt (wt%) |
|---|---|---|
| EXAMPLE 5 | 90 | 10 |
| EXAMPLE 6 | 50 | 50 |
| EXAMPLE 7 | 10 | 90 |
| COMPARATIVE EXAMPLE 2 | 90 | 10 |

NOX-DECOMPOSING ELECTRODE AND NOX CONCENTRATION-MEASURING APPARATUS

BACKGROUND OF THE INVENTION

1. Field of the Invention

The present invention relates to a NOx-decomposing electrode, i.e., an electrode for decomposing or reducing NOx, especially for decomposing NOx to produce oxygen, and to a NOx concentration-measuring apparatus for measuring NOx contained in the atmospheric air or in the exhaust gas discharged from vehicles or automobiles.

2. Description of the Related Art

A method has been hitherto known, in which NOx contained in a measurement gas is detected by measuring an electromotive force generated on a NOx-decomposing electrode when an exhaust gas discharged from a vehicle or an automobile is introduced as the measurement gas into a sensor which includes the NOx-decomposing electrode (see Japanese Laid-Open Patent Publication No. 2000-171436). In this technique, the NOx-decomposing electrode is a cermet electrode composed of an alloy of Pt—Rh and a ceramic component. The NOx-decomposing electrode is formed on an oxygen ion-conductive solid electrolyte such as zirconia.

A ratio between Pt and Rh (Pt:Rh) in the NOx-decomposing electrode ranges from 20:80 to 1:99 or from 10:90 to 1:99 by weight ratio. When above ratio is adopted, the oxidation reaction and the reduction reaction of Rh are suppressed on the NOx-decomposing electrode. Further, the adsorption of NOx to the NOx-decomposing electrode, which is used at a low temperature, is suppressed, and the alloy formation between the NOx-decomposing electrode and another metal element (for example, Au) is suppressed. Therefore, a NOx concentration-measuring apparatus, which uses the NOx-decomposing electrode as described above, the stabilization of the impedance of the pumping cell and the stabilization of the sensitivity of measurement of NOx.

It is demanded for such a NOx-decomposing electrode that the ability to decompose NOx is high and the oxidation reaction and the reduction reaction can be suppressed. In such a case, the ability to decompose NOx is improved by increasing a ratio of Rh in the Pt—Rh alloy so that the ratio is larger than a ratio of Pt in the Pt—Rh alloy. On the other hand, the oxidation reaction and the reduction reaction are suppressed by increasing the ratio of Pt in the Pt—Rh alloy so that the ratio of Pt in the Pt—Rh alloy is larger than the ratio of Rh in the Pt—Rh alloy. Therefore, it is impossible to realize the improvement of the ability to decompose NOx and the suppression of the oxidation reaction and the reduction reaction in the NOx-decomposing electrode as described above.

Further, the NOx-decomposing electrode measures NOx at a high temperature of 700° C. to 800° C. Therefore, the NOx-decomposing electrode repeats thermal expansion and thermal contraction every time when NOx is measured. As a result, the NOx-decomposing electrode is exfoliated from the solid electrolyte, and the ability of the NOx concentration-measuring apparatus to measure NOx is lowered.

SUMMARY OF THE INVENTION

An object of the present invention is to provide a NOx-decomposing electrode and a NOx concentration-measuring apparatus comprising a plurality of the cermet electrode layers having different ratios between an alloy comprised Pt and Rh and a ceramic component to increase the adhesion between cermet electrode layers and a solid electrolyte, so that the NOx-decomposing electrode and the NOx concentration-measuring apparatus have high reliability and durability.

According to the present invention, there is provided a NOx-decomposing electrode, i.e., an electrode for decomposing or reducing NOx, especially for decomposing NOx to produce oxygen; wherein the NOx-decomposing electrode has a plurality of cermet electrode layers each of which comprise an alloy of Pt—Rh and a ceramic component; and the respective cermet electrode layers have different ratios between the alloy of Pt—Rh and the ceramic component. The ceramic component is preferably partially stabilized $ZrO_2$ or fully stabilized $ZrO_2$. A stabilizer may be used, including, for example, $Y_2O_3$, MgO, CaO, and $CeO_2$. However, it is especially preferable to use $Y_2O_3$ in view of the sintering at a low temperature.

The NOx-decomposing electrode is formed on a ceramic substrate. Proportions of the alloy of Pt—Rh in the respective cermet electrode layers of the NOx-decomposing electrode are established such that the proportion is minimum in the cermet electrode layer which is disposed at a lowermost layer of the electrode and which is formed directly on the ceramic substrate and the proportion is maximum in the cermet electrode layer which is an uppermost layer of the electrode. It is preferable that the material for the ceramic substrate are the same as the material for the NOx-decomposing electrode. It is preferable to use partially stabilized $ZrO_2$ or fully stabilized $ZrO_2$. A stabilizer may be used, including, for example, $Y_2O_3$, MgO, CaO, and $CeO_2$. However, it is especially preferable to use $Y_2O_3$ in view of the sintering at a low temperature.

That is, in the NOx-decomposing electrode, a ratio of the alloy of Pt—Rh in the lower cermet electrode layer is small as compared with a ratio of the alloy of Pt—Rh in the upper cermet electrode layer. Specifically, the lower cermet electrode layer, which is formed near to the ceramic substrate, has such a ratio that an amount of the ceramic component is larger than an amount of the alloy of Pt—Rh. On the other hand, the upper cermet electrode layer has such a ratio that the amount of the alloy of Pt—Rh is larger than the amount of the ceramic component.

Accordingly, the amount of the ceramic component is larger than the amount of the alloy of Pt—Rh in the cermet electrode layer disposed at the lowermost layer which is formed directly on the ceramic substrate. Therefore, the adhesion between the ceramic substrate and the cermet electrode layer disposed at the lowermost layer is increased. Accordingly, it is prevented that the NOx-decomposing electrode is exfoliated from the ceramic substrate. Therefore, the NOx-decomposing electrode has high reliability and a long service life.

In particular, the NOx-decomposing electrode comprises a first cermet electrode layer which is formed on the ceramic substrate and a second cermet electrode layer which is formed on the first cermet electrode layer; the ratio between the alloy of Pt—Rh and the ceramic component ((alloy of Pt—Rh):(ceramic component)) in the first cermet electrode layer ranges from 20:80 to 50:50 by volume ratio; and the ratio between the alloy of Pt—Rh and the ceramic component ((alloy of Pt—Rh):(ceramic component)) in the second cermet electrode layer ranges from 60:40 to 50:50 by volume ratio. On this condition, the adhesive force of the NOx-decomposing electrode with respect to the ceramic substrate is further enhanced. Specifically, the adhesive force between the ceramic substrate and the NOx-decomposing electrode of the present invention is increased not less than twice in comparison with the adhesive force between the ceramic substrate and the conventional NOx-decomposing electrode. As a result, the service life of the NOx-decomposing electrode of the present invention is not less than twice the service life of the conventional NOx-decomposing electrode.

In this arrangement, it is preferable that ratios between Pt and Rh (Pt:Rh) of the respective cermet electrode layers range from 10:90 to 90:10 by weight ratio. On this condition, when the proportion of Pt is increased in the first cermet electrode layer and the second cermet electrode layer, thermal expansion and thermal contraction in the NOx-decomposing electrode are suppressed. Therefore, it is prevented that the NOx-decomposing electrode is exfoliated from the ceramic substrate during the measurement of the NOx concentration.

According to another aspect of the present invention, there is provided a NOx concentration-measuring apparatus comprising a first oxygen pump means for introducing a measurement gas from the outside of the apparatus into a first hollow space provided in the NOx concentration-measuring apparatus to adjust a partial pressure of oxygen in the measurement gas; and a second oxygen pump means for pumping out oxygen contained in the measurement gas from the measurement gas having the partial pressure of oxygen controlled by the first oxygen pump means and controlling the partial pressure of oxygen to have a predetermined value at which a NOx component is reduced or decomposed to pump out oxygen produced when the NOx component contained in an atmosphere in a second hollow space provided in the NOx concentration-measuring apparatus is reduced or decomposed; wherein a concentration of NOx in the measurement gas is detected by measuring a pumping current flowing through the NOx concentration-measuring apparatus in accordance with a pumping action of the second oxygen pump means. In this arrangement, a NOx-decomposing electrode of the second oxygen pump means for reducing or decomposing the NOx component has a plurality of cermet electrode layers each of which comprise an alloy of Pt—Rh and a ceramic component. Further, the respective cermet electrode layers have different ratios between the alloy of Pt—Rh and the ceramic component.

The above and other objects, features, and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 3 is a table illustrating a ratio between the alloy and $ZrO_2$ in first cermet electrode layers of NOx-decomposing electrodes according to a first experiment;

FIG. 5 is a table illustrating a ratio between Pt and Rh in first and second cermet electrode layers of NOx-decomposing electrodes according to a second experiment;

DESCRIPTION OF THE PREFERRED EMBODIMENTS

Preferred embodiments of the NOx concentration-measuring apparatus 10 according to the present invention will be explained with reference to FIGS. 1 to 7.

Figure 1:
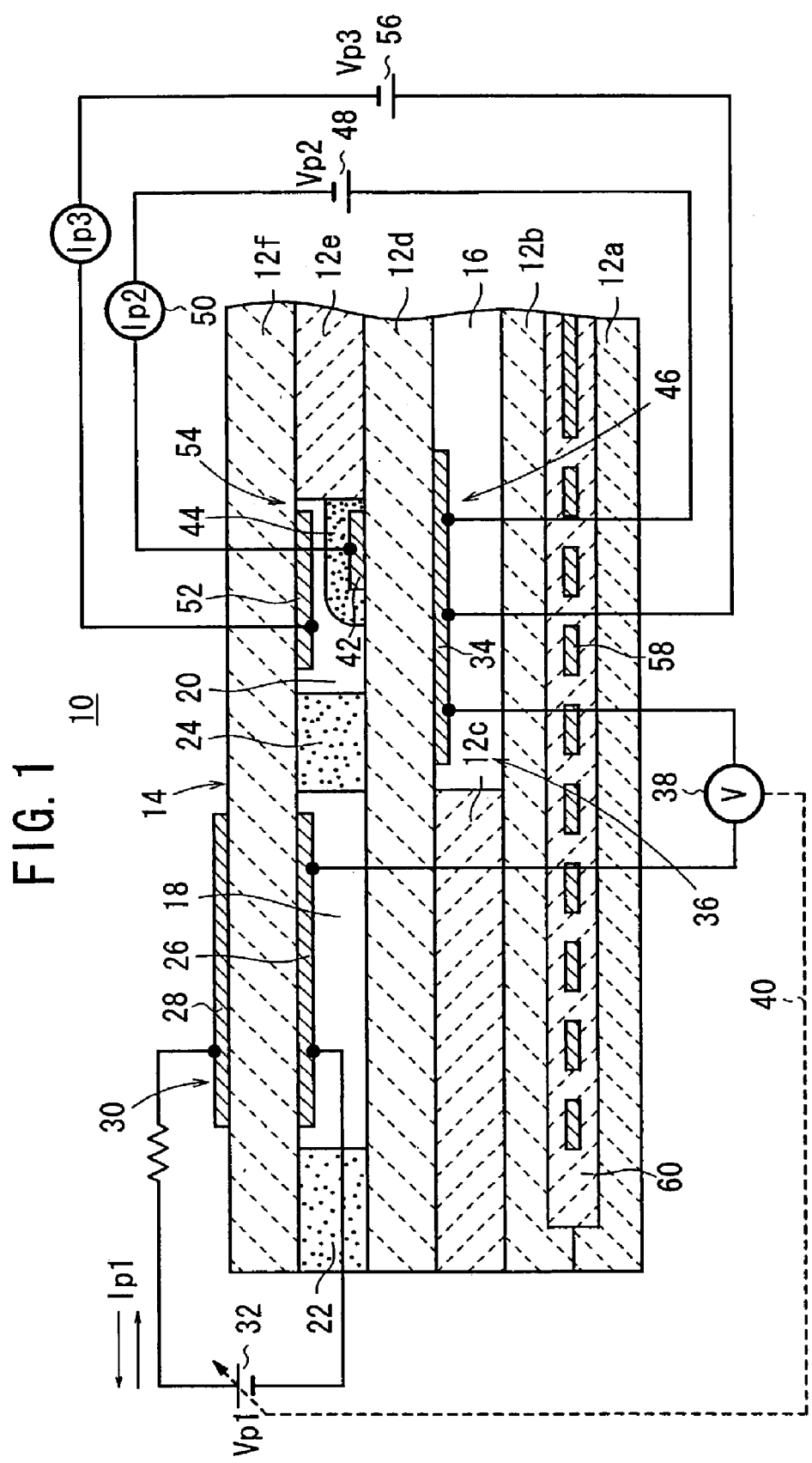
FIG. 1 is a longitudinal sectional view illustrating a NOx concentration-measuring apparatus according to an embodiment of the present invention.

As shown in FIG. 1, a NOx concentration-measuring apparatus 10 has a substrate 14 comprising six laminated solid electrolyte layers 12a to 12f which are ceramics of oxygen ion-conductive solid electrolyte such as $ZrO_2$.

A space (space for introducing reference gas 16), into which a reference gas, for example, the atmospheric air to serve as a reference to measure the oxide is introduced, is formed by the solid electrolyte layers 12b, 12c, 12d in the substrate 14.

The substrate 14 is formed with a first chamber 18 for adjusting the partial pressure of oxygen in the measurement gas, and a second chamber 20 for finely adjusting the partial pressure of oxygen in the measurement gas and measuring the oxide, for example, nitrogen oxides (NOx) in the measurement gas.

In the NOx concentration-measuring apparatus 10, the first chamber 18 of the solid electrolyte layer 12e is communicated with the outside via a first diffusion rate-determining section 22. The first chamber 18 and the second chamber 20 are communicated with each other via a second diffusion rate-determining section 24.

The first and second diffusion rate-determining sections 22, 24 give predetermined diffusion resistances to the measurement gas to be introduced into the first chamber 18 and the second chamber 20 respectively. As shown in FIG. 1, each of the first and second diffusion rate-determining sections 22, 24 is formed as a rectangular slit for introducing the measurement gas. Both of the slits are formed in the solid electrolyte layer 12e.

The slit for constituting the second diffusion rate-determining section 24 may be filled with a porous member composed of $ZrO_2$ or the like so that the diffusion resistance of the second diffusion rate-determining section 24 is larger than the diffusion resistance of the first diffusion rate-determining section 22.

A part of the atmosphere in the first chamber 18, to which the predetermined diffusion resistance is applied by the second diffusion rate-determining section 24, is introduced into the second chamber 20.

The second diffusion rate-determining section 24 restricts the amount of oxygen in the measurement gas to inflow into the measuring space (second chamber 20) from the first chamber 18. Accordingly, when a constant DC voltage Vp3 is applied to an auxiliary pumping cell 54 as described later on, a pumping current Ip3, which flows through the auxiliary pumping cell 54, is suppressed.

The NOx concentration-measuring apparatus 10 according to the embodiment of the present invention further comprises a pumping electrode 26 which comprises a porous cermet electrode (for example, a cermet electrode of Pt—ZrO$_2$ containing 1% by weight of Au) and which is provided on the inner wall surface of the first chamber 18. A pumping electrode 28, which is opposed to the pumping electrode 26, is provided on the upper surface of the solid electrolyte layer 12f. An electrochemical pumping cell, i.e., a main pumping cell 30 is constructed by the pumping electrodes 26, 28 and the solid electrolyte layers 12d, 12e, 12f.

When a desired control voltage (pumping voltage) Vp1 is applied to the pumping electrodes 26, 28 of the main pumping cell 30 from a variable DC power source 32 provided at the outside of the NOx concentration-measuring apparatus 10, a pumping current Ip1 flows through the solid electrolyte layer 12f disposed between the pumping electrodes 26, 28. When the pumping current Ip1 flows, then the oxygen in the atmosphere in the first chamber 18 can be pumped out to the outside of the apparatus 10, or the oxygen can be pumped into the first chamber 18 from the outside of the apparatus 10.

A reference electrode 34 is formed at a portion of the lower surface of the solid electrolyte layer 12d for forming the space 16. An electrochemical sensor cell, i.e., a cell for controlling and detecting oxygen partial pressure 36 is constructed by the pumping electrode 26, the reference electrode 34, and the solid electrolyte layer 12d.

The cell 36 detects the partial pressure of oxygen contained in the atmosphere in the first chamber 18 by measuring, with a voltmeter 38, the electromotive force generated between the pumping electrode 26 and the reference electrode 34 on the basis of the difference in oxygen concentration between the atmosphere in the first chamber 18 and the reference gas (atmospheric air) in the space 16.

That is, the voltage V1, which is generated between the pumping electrode 26 and the reference electrode 34, is the electromotive force which is generated on the basis of the difference between the partial pressure of oxygen of the reference gas introduced into the space 16 and the partial pressure of oxygen of the measurement gas in the first chamber 18. The partial pressure of oxygen in the first chamber 18 can be detected due to measuring the voltage V1 by means of the voltmeter 38.

A feedback control system 40 controls the pumping voltage of the variable power source 32 by using the voltage corresponding to the partial pressure of oxygen detected as described above. That is, the feedback system 40 controls the pumping action of the main pumping cell 30 so that the partial pressure of oxygen in the atmosphere in the first chamber 18 has a predetermined value. Accordingly, it is possible to control the partial pressure of oxygen in the second chamber 20.

Each of the pumping electrodes 26, 28 comprise an inert material having low catalytic activity on NOx, for example, NO contained in the measurement gas introduced into the first chamber 18.

In the NOx concentration-measuring apparatus 10 according to the embodiment of the present invention, a detecting electrode 42, which comprises a substantially rectangular porous cermet electrode, is formed at a portion of the upper surface of the solid electrolyte layer 12d for forming the second chamber 20, the portion being separated from the second diffusion rate-determining section 24. The detecting electrode 42 is coated with an alumina film which constitutes a third diffusion rate-determining section 44. An electrochemical pumping cell, i.e., a measuring pumping cell 46 is constructed by the detecting electrode 42, the reference electrode 34, and the solid electrolyte layer 12d.

When a constant DC voltage Vp2 is applied by a DC power source 48 between the reference electrode 34 and the detecting electrode 42 of the measuring pumping cell 46, the oxygen in the atmosphere in the second chamber 20 can be pumped out to the space 16. A pumping current Ip2, which flows in accordance with the pumping action of the measuring pumping cell 46, is detected by an ampere meter 50. Details of the detecting electrode 42 will be described later on.

When the inflow of NOx is restricted by the third diffusion rate-determining section 44, the constant voltage (DC) power source 48 applies a voltage to the third diffusion rate-determining section 44 in which a limiting current corresponding to the pumping of oxygen generated during the decomposition of NOx in the measuring pumping cell 46 flows.

On the other hand, an auxiliary pumping electrode 52, which comprises a porous cermet electrode (for example, a cermet electrode of Pt—ZrO$_2$ containing 1% by weight of Au), is formed at a portion of the lower surface of the solid electrolyte layer 12f for forming the inner wall surface of the second chamber 20. An auxiliary electrochemical pumping cell, i.e., an auxiliary pumping cell 54 is constructed by the auxiliary pumping electrode 52, the solid electrolyte layers 12d, 12e, 12f, and the reference electrode 34.

A material, which does not reduce the NO component in the measurement gas, is used for the auxiliary pumping electrode 52 in the same manner as for the pumping electrode 26 of the main pumping cell 30.

When the constant DC voltage Vp3 is applied between the reference electrode 34 and the auxiliary pumping electrode 52 of the auxiliary pumping cell 54 by a DC power source 56 provided at the outside of the apparatus 10, the oxygen contained in the atmosphere in the second chamber 20 can be pumped out to the space 16.

Accordingly, the partial pressure of oxygen in the atmosphere in the second chamber 20 is lowered to such a value that the measurement of the amount of the NOx component is not affected thereby when the measurement gas component (NOx) is not reduced or decomposed. In this arrangement, the amount of change of oxygen to be introduced into the second chamber is extremely low as compared with the amount of change in the measurement gas, owing to the main pumping cell 30 disposed for the first chamber 18. Accordingly, the partial pressure of oxygen in the second chamber 20 is controlled to have a constant value.

Therefore, in the NOx concentration-measuring apparatus 10 as described above, the measurement gas, for which the partial pressure of oxygen has been controlled in the second chamber 20, is introduced into the detecting electrode 42.

The NOx concentration-measuring apparatus 10 according to the embodiment of the present invention comprises a plurality of heaters 58 for generating the heat in accordance with the supply of the electric power from the outside of the apparatus 10, the heaters 58 being embedded under the solid electrolyte layer 12b. The heaters 58 are provided in order to enhance the oxygen ion conductivity in the NOx concentration-measuring apparatus 10. In this arrangement, in order to electrically insulate the heaters 58 from the solid electrolyte layers 12a, 12b, an insulating layer 60 comprised alumina or the like is filled around the heaters 58.

The heaters 58 are arranged opposite an area ranging from the first chamber 18 to the second chamber 20. Accordingly, the first chamber 18 and the second chamber 20 are heated to a predetermined temperature. The main pumping cell 30, the cell 36, and the measuring pumping cell 46 are also heated to a predetermined temperature by the heaters 58.

Figure 2:
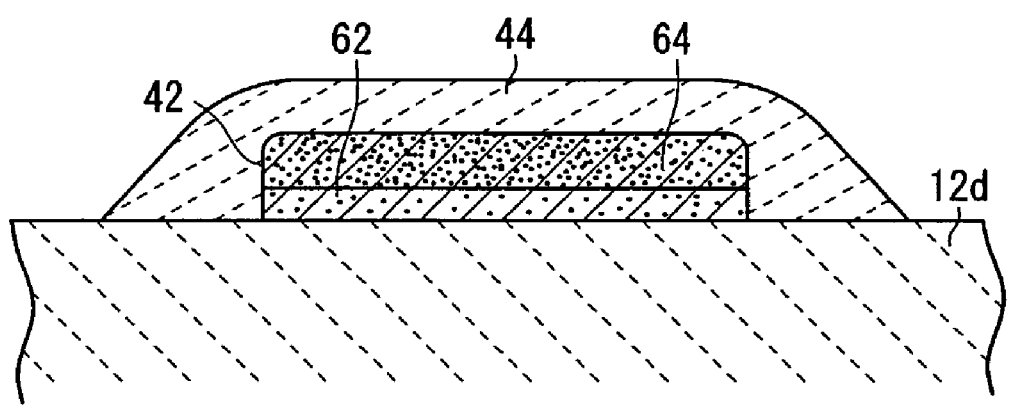
FIG. 2 is a vertical sectional view illustrating a NOx-decomposing electrode according to the embodiment of the present invention.

As shown in FIG. 2, the detecting electrode 42 of the NOx concentration-measuring apparatus 10 according to the embodiment of the present invention has a first cermet electrode layer 62 which is formed directly on the solid electrolyte layer 12d as the substrate, and a second cermet electrode layer 64 which is formed on the first cermet electrode layer 62. Each of the first cermet electrode layer 62 and the second cermet electrode layer 64 is contained a ceramic component of porous cermet comprising $ZrO_2$ and an alloy of Pt—Rh.

The first cermet electrode layer 62 and the second cermet electrode layer 64 are formed so that a ratio between the alloy of Pt—Rh and $ZrO_2$ ((alloy of Pt—Rh):(ceramic component)) differs therebetween. Specifically, the ratio between the alloy of Pt—Rh and $ZrO_2$ in the first cermet electrode layer 62 ranges from 20:80 to 50:50 by volume ratio. On the other hand, the ratio between the alloy of Pt—Rh and $ZrO_2$ ((alloy of Pt—Rh):(ceramic component)) ranges form 60:40 to 50:50 by volume ratio.

As described above, in the first cermet electrode layer 62, the ratio is established so that the amount of the alloy of Pt—Rh is the same as the amount of $ZrO_2$, or the amount of the alloy of Pt—Rh is larger than the amount of $ZrO_2$. Accordingly, the adhesion between the first cermet electrode layer 62 and the solid electrolyte layer 12d which comprises the ceramic material ($ZrO_2$) is increased. Further, it is prevented that the detecting electrode 42 is exfoliated from the solid electrolyte layer 12d.

It is preferable that the ratio between Pt and Rh (Pt:Rh) in the first cermet electrode layer 62 and the second cermet electrode layer 64 ranges from 10:90 to 90:10 by weight ratio. As for the ratio between Pt and Rh, when the proportion of Pt is increased in the first cermet electrode layer 62 and the second cermet electrode layer 64, then thermal expansion and thermal contraction of the detecting electrode 42 are suppressed, and it is prevented that the detecting electrode 42 is exfoliated from the solid electrolyte layer 12d during the measurement of the NOx concentration.

The basic operation of the NOx concentration-measuring apparatus 10 according to the embodiment of the present invention is the same as or equivalent to that of the NOx concentration-measuring apparatus disclosed in Japanese Laid-Open Patent Publication No. 11-183434, any further explanation of which is omitted herein.

Two experiments will now be described.

The first experiment is an investigation on the exfoliation of the detecting electrode 42 from the solid electrolyte layer 12d (see FIG. 2), i.e., a defect ratio F(t) of the NOx concentration-measuring apparatus 10 according to the embodiment of the present invention with respect to the number of cycle of the operation and the operation stop of the apparatus 10 when the operation and the operation stop were repeated at a high temperature, in relation to the ratio between the alloy of Pt—Rh and $ZrO_2$ in the first cermet electrode layer 62.

As shown in FIG. 3, NOx concentration-measuring apparatuses 10 (Examples 1 to 4) according to the embodiment of the present invention including first cermet electrode layers 62 having different ratios between the alloy of Pt—Rh and $ZrO_2$, and a NOx concentration-measuring apparatus (Comparative Example 1) including a conventional detecting electrode were provided in the first experiment,.

Next, an explanation will be made about a method for producing the NOx concentration-measuring apparatuses 10 (Examples 1 to 4) of the first experiment.

At first, a paste for the first cermet electrode layer 62 is prepared. An alloy, in which the ratio between Rh and Pt (Rh:Pt) is 90:10 by weight ratio, is used as the alloy of Pt—Rh. The alloy of Pt—Rh and $ZrO_2$ are blended so that the ratio between the alloy of Pt—Rh and $ZrO_2$ is the ratio as shown in FIG. 3. Further, an organic binder, a plasticizer, and an organic solvent are added to a concoction blended by the alloy of Pt—Rh and $ZrO_2$ to prepare the paste for the first cermet electrode layer 62.

Subsequently, a paste for the second cermet electrode layer 64 is prepared. In this case, an alloy, in which the ratio between Rh and Pt (Rh:Pt) is 90:10 by weight ratio, is used as the alloy of Pt—Rh. The alloy of Pt—Rh and $ZrO_2$ are blended so that the ratio between the alloy of Pt—Rh and $ZrO_2$ ((alloy of Pt—Rh):(ceramic component)) is 60:40. Further, an organic binder, a plasticizer, and an organic solvent are added to a concoction blended by the alloy of Pt—Rh and $ZrO_2$ to prepare the paste for the second cermet electrode layer 64.

Subsequently, a green sheet of the solid electrolyte layer 12d is prepared. The green sheet is prepared by mixing a powder of partially stabilized zirconia or fully stabilized zirconia, an organic binder, a plasticizer, and an organic solvent, and performing, for example, the doctor blade method.

Subsequently, the paste for the first cermet electrode layer 62 is applied to have a thickness of 5 to 15 μm on the green sheet of the solid electrolyte layer 12d by the screen printing, and thus a pattern of the first cermet electrode layer 62 is formed on the green sheet.

Subsequently, the paste for the second cermet electrode layer 64 is applied to have a thickness of 15 to 25 μm on the first cermet electrode layer 62 by the screen printing, and thus a pattern of the second cermet electrode layer 64 is formed on the first cermet electrode layer 62.

Subsequently, an alumina paste is applied to have a thickness of 20 to 50 μm by the screen printing so that the entire detecting electrode 42 is covered with the alumina paste.

A pattern of the reference electrode 34 is formed on the green sheet of the solid electrolyte layer 12d in addition to the pattern of the detecting electrode 42. Respective patterns of the pumping electrodes 26, 28 and the auxiliary pumping electrode 52 are formed on the green sheets of the solid electrolyte layers 12d, 12f. Further, the green sheets as described above are laminated to obtain a laminate.

Subsequently, the laminate is sintered at a high temperature of not less than 1300° C. to obtain the substrate 14. The electrodes including the detecting electrode 42 as described above are formed on the substrate 14 by the sintering.

Subsequently, for example, a housing, a protective cover, and a connector, which are not shown in FIG. 1, are provided on the substrate 14 to obtain each of the NOx concentration-measuring apparatuses 10 (Examples 1 to 4) of the first experiment.

On the other hand, in the case of the NOx concentration-measuring apparatus (Comparative Example 1) including the conventional detecting electrode, an alloy in which the ratio between Rh and Pt (Rh:Pt) is 90:10 by weight ratio, is used. A paste for the detecting electrode is prepared by blending the alloy of Pt—Rh and a ceramic component ((alloy of Pt—Rh):(ceramic component)) is 60:40 by volume ratio, and adding an organic binder, a plasticizer, and an organic solvent thereto. The paste for the detecting electrode is applied to have a thickness of 20 to 40 μm on a green sheet of $ZrO_2$ by the screen printing to form a pattern of the detecting electrode. The pattern of the detecting electrode is sintered to obtain the detecting electrode. Therefore, the conventional NOx concentration-measuring apparatus (Comparative Example 1) is produced in accordance with the same method as that used for the NOx concentration-measuring apparatuses 10 (Examples 1 to 4) of the first experiment except for the method for producing the detecting electrode.

Next, an explanation will be made about a method for measuring the defect ratio F(t) for the NOx concentration-measuring apparatuses 10 (Examples 1 to 4) of the first experiment.

At first, each of the NOx concentration-measuring apparatuses 10 (Examples 1 to 4) of the first experiment is arranged in an electric furnace. Subsequently, an interior of the electric furnace is adjusted to a high temperature atmosphere so that the NOx concentration-measuring apparatus 10 (Examples 1 to 4) is in a state of 700 to 800° C. In this state, the operation and the operation stop of the main pumping cell 30, the measuring pumping cell 46, the auxiliary pumping cell 54, and the heaters 58 of the NOx concentration-measuring apparatus 10 are repeated. The period of time for the operation is 5 minutes, and the period of time for the operation stop is 5 minutes.

When the operation and the operation stop are repeated within 1000 cycles, the NOx sensitivity of the detecting electrode 42, i.e., the pumping current Ip2 is measured by the ampere meter 50 at every 100 cycles. When the repetition is performed by not less than 1000 cycles, the NOx sensitivity of the detecting electrode 42 is measured at every 500 cycles.

When the measured NOx sensitivity is less than 20% of the NOx sensitivity previously measured before performing the experiment, then it may be thought that the exfoliation of the detecting electrode 42 from the solid electrolyte layer 12d occurs, and cracks appear in the alumina film of the third diffusion rate-determining section 44. Based on this result, it is judged that the NOx concentration-measuring apparatus 10 (Examples 1 to 4) of the embodiment of the present invention is deteriorated. The NOx concentration-measuring apparatus 10 is disassembled, and the cross section of the detecting electrode 42 is observed by using an electron microscope to confirm whether the cracks are present or not.

Figure 4:
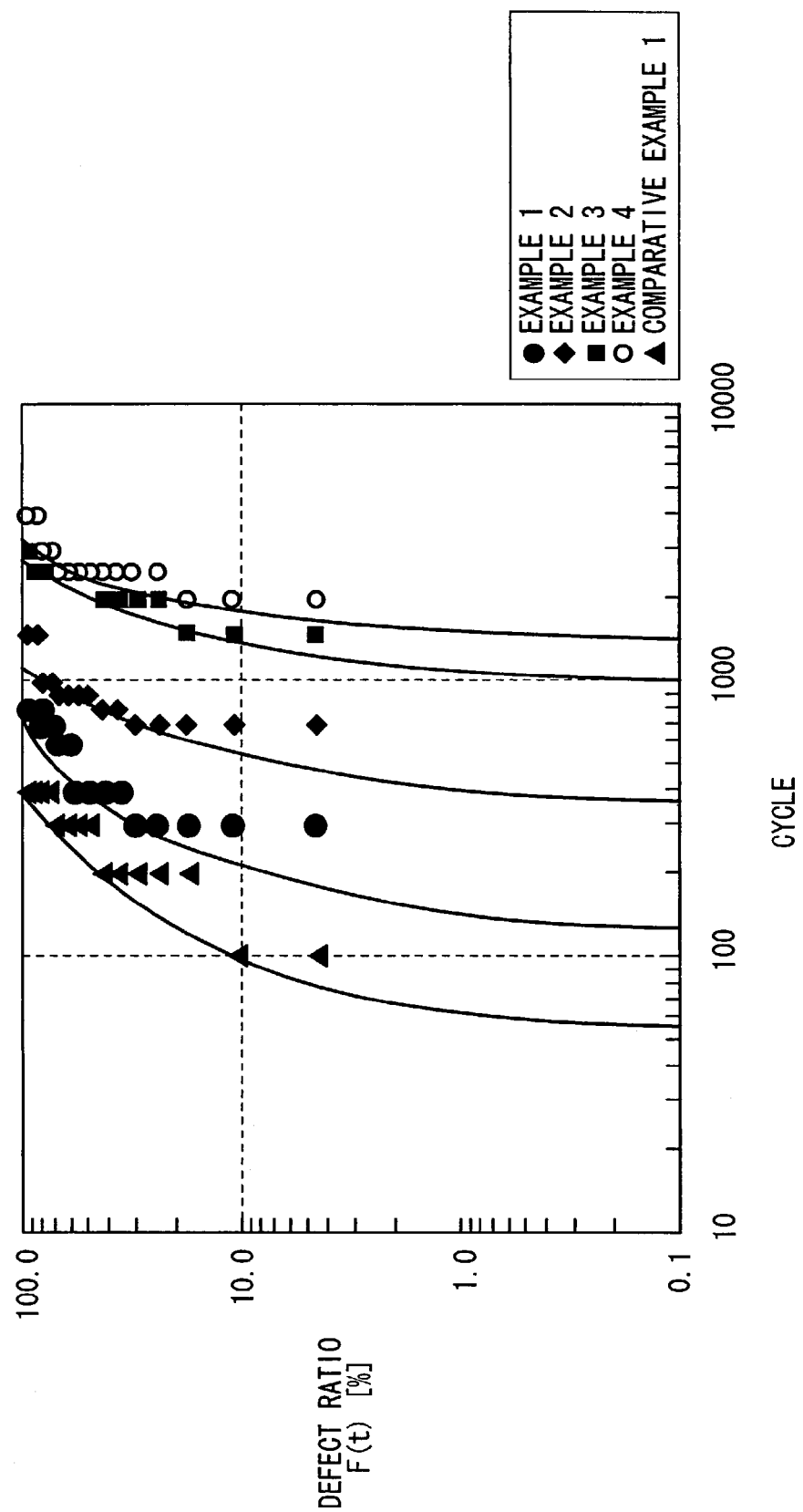
FIG. 4 is a Weibull plot illustrating a defect ratio of the NOx concentration-measuring apparatus according to the first experiment.

The defect ratio F(t) is defined as the number of the NOx concentration-measuring apparatuses 10 in which the appearance of cracks is confirmed, of the number of the disassembled NOx concentration-measuring apparatuses 10 to prepare a Weibull plot as shown in FIG. 4.

The defect ratio F(t) of the conventional NOx concentration-measuring apparatus (Comparative Example 1) was measured in accordance with the same measuring method as the measuring method for the NOx concentration-measuring apparatuses 10 (Examples 1 to 4) of the first experiment described above.

FIG. 4 shows the plots of those of Examples 1 to 4 and Comparative Example 1 which were judged to be deteriorated at the lowest cycles, of the NOx concentration-measuring apparatuses 10 (Examples 1 to 4) of the first experiment and the conventional NOx concentration-measuring apparatuses (Comparative Example 1) which were judged to be deteriorated.

The first experiment results in F(t)=0.1% at about 50 cycles in Comparative Example 1, F(t)=0.1% at about 110 cycles in Example 1, F(t)=0.1% at about 400 cycles in Example 2, F(t)=0.1% at about 1000 cycles in Example 3, and F(t)=0.1% at about 1200 cycles in Example 4. That is, the defect ratio F(t) in the Examples 1 to 4 is small and the service life of the Examples 1 to 4 is long as compared with Comparative Example 1.

With reference to FIG. 3, the proportion of $ZrO_2$, by which the first cermet electrode layer 62 is occupied, is smallest in Example 1, and it is largest in Example 4. When the results shown in FIGS. 3 and 4 are considered, the exfoliation of the detecting electrode 42 from the solid electrolyte layer 12d is hardly caused as the proportion of $ZrO_2$, by which the first cermet electrode layer 62 is occupied, becomes large. Therefore, the NOx concentration-measuring apparatus 10 of the embodiment of the present invention is the NOx concentration-measuring apparatus which has the high reliability and the long service life.

Next, the second experiment is an investigation on the defect ratio F(t) of the NOx concentration-measuring apparatus 10 of the embodiment of the present invention with respect to the change of the ratio between Pt and Rh in the alloy of Pt—Rh for constituting the first cermet electrode layer 62.

In the second experiment, as shown in FIG. 5, three NOx concentration-measuring apparatuses 10 (Examples 5 to 7) provided with the first and second cermet electrode layers 62, 64 having different ratios between Pt and Rh, and a NOx concentration-measuring apparatus (Comparative Example 2) provided with the conventional detecting electrode were manufactured.

The method for producing the NOx concentration-measuring apparatuses 10 (Examples 5 to 7) of the second experiment is the same as the producing method used the first experiment except that the ratio between the alloy of Pt—Rh and $ZrO_2$ ((alloy of Pt—Rh):$ZrO_2$) in the first cermet electrode layer 62 is 30:70 by volume ratio, and the ratio between the alloy of Pt—Rh and $ZrO_2$ ((alloy of Pt—Rh):$ZrO_2$) in the second cermet electrode layer 64 is 60:40 by volume ratio.

On the other hand, the NOx concentration-measuring apparatus (Comparative Example 2), which has the conventional detecting electrode, uses the same detecting electrode as that used in Comparative Example 1. Therefore, the NOx concentration-measuring apparatus (Comparative Example 2) concerning the conventional technique is produced in accordance with the same method as that used in Comparative Example 1 in the first experiment.

The method for measuring the defect ratio F(t) for the NOx concentration-measuring apparatuses 10 (Examples 5 to 7) of the second experiment and the conventional NOx concentration-measuring apparatus (Comparative Example 2) is the same as the measuring method used for the NOx concentration-measuring apparatuses 10 (Examples 1 to 4) in the first experiment.

Figure 6:
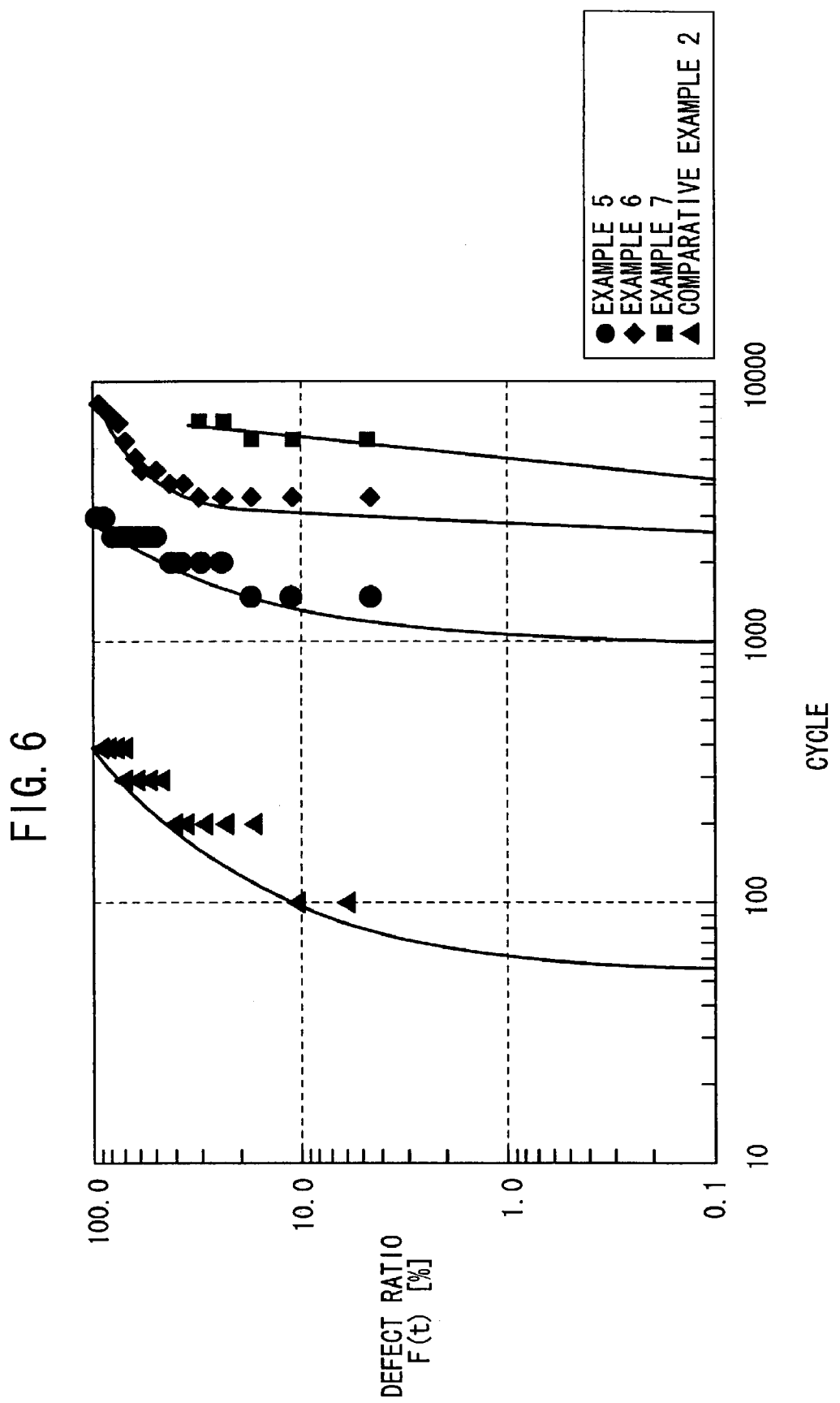
FIG. 6 is a Weibull plot illustrating a defect ratio of the NOx concentration-measuring apparatus according to the second experiment.

FIG. 6 shows the plots of those of Examples 5 to 7 and Comparative Example 2 which were judged to be deteriorated at the lowest cycles, of the NOx concentration-measuring apparatuses 10 (Examples 5 to 7) of the second experiment and the conventional NOx concentration-measuring apparatuses (Comparative Example 2) which were judged to be deteriorated.

The second experiment results in F(t)=0.1% at about 50 cycles in Comparative Example 2, F(t)=0.1% at about 1000 cycles in Example 5, F(t)=0.1% at about 2300 cycles in Example 6, and F(t)=0.1% at about 4000 cycles in Example 7. That is, the defect ratio F(t) in Examples 5 to 7 is small and the service life of Examples 5 to 7 is long as compared with Comparative Example 2.

In Examples 5 to 7, the proportion of $ZrO_2$ in the first cermet electrode layer 62 is higher than the proportion of $ZrO_2$ in the second cermet electrode layer 64. Therefore, the exfoliation of the detecting electrode 42 from the solid electrolyte layer 12d is hardly caused in Examples 5 to 7 as compared with Comparative Example 2.

With reference to FIG. 5, the proportion of Pt, by which the first cermet electrode layer 62 is occupied, is smallest in Example 5, and it is largest in Example 7. When the results shown in FIGS. 5 and 6 are considered, the exfoliation of the detecting electrode 42 from the solid electrolyte layer 12d is hardly caused as the proportion of Pt, by which the first cermet electrode layer 62 is occupied, becomes large.

Therefore, the NOx concentration-measuring apparatus 10 of the embodiment of the present invention is the NOx concentration-measuring apparatus which has the high reliability and the long service life.

The embodiment described above is illustrative of the case in which the cermet electrode layer for constituting the detecting electrode 42 has the two electrode layers. The cermet electrode layer of the detecting electrode 42 is not limited to the two electrode layers as described above. The cermet electrode layer of the detecting electrode 42 may be formed to have three or more electrode layers. In this arrangement, the proportion of the alloy of Pt—Rh is maximum in the cermet electrode layer disposed at the uppermost layer. Accordingly, it is possible to increase the adhesion between the solid electrolyte layer 12d and the detecting electrode 42.

Figure 7:
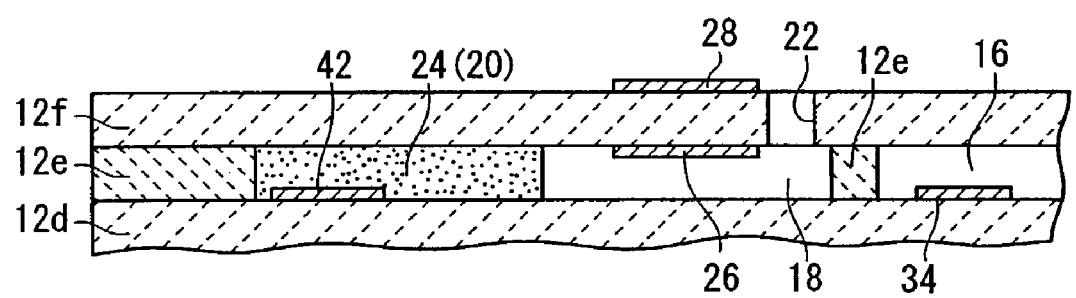
FIG. 7 is a longitudinal sectional view illustrating a modified embodiment of the NOx concentration-measuring apparatus according to the embodiment of the present invention.

As shown in FIG. 7, the second chamber 20 and the second diffusion rate-determining section 24 may be filled with a porous member as a modified embodiment of the NOx concentration-measuring apparatus 10 according to the embodiment of the present invention. More specifically, the second chamber 20 and the second diffusion rate-determining section 24 are changed to have the structure shown in FIG. 7 in the NOx concentration-measuring apparatus 10 according to the embodiment of the present invention shown in FIG. 1. That is, a second diffusion rate-determining section 24, which comprises a porous member such as porous alumina, is formed in a hollow space which is communicated with the first chamber 18. The second diffusion rate-determining section 24 is constituted as the second chamber 20. Accordingly, it is possible to simplify the internal structure of the NOx concentration-measuring apparatus 10.

The diffusion resistance of the second diffusion rate-determining section 24 is larger than the diffusion resistance of the first diffusion rate-determining section 22. Therefore, the atmosphere in the first chamber 18 is not affected by the atmosphere in the second chamber 20.

It is a matter of course that the NOx-decomposing electrode and the NOx concentration-measuring apparatus of the present invention are not limited to the embodiments described above, which may be embodied in other various forms without deviating from the gist or essential characteristics of the present invention.

What is claimed is:

1. A NOx-decomposing electrode for reducing NOx or decomposing to NOx to produce oxygen, said NOx-decomposing electrode comprising a plurality of cermet electrode layers each of which comprises an alloy of Pt—Rh and a ceramic component, a first of said cermet electrode layers being formed on a ceramic substrate, and a second of said cermet electrode layers being formed on said first cermet electrode layer, wherein said respective cermet electrode layers have different ratios between said alloy of Pt—Rh and said ceramic component, wherein said ratio between said alloy of Pt—Rh and said ceramic component in said first cermet electrode layer ranges from 20:80 to 50:50 by volume ratio, wherein said ratio between said alloy of Pt—Rh and said ceramic component in said second cermet electrode layer ranges from 60:40 to 50:50 by volume ratio, and wherein proportions of said alloy of Pt—Rh in said respective cermet electrode layers are established such that said proportion is minimum in said first cermet electrode layer, which is a lowermost layer of said electrode, and maximum in said second cermet electrode layer, which is an uppermost layer of said electrode.

2. The NOx-decomposing electrode according to claim 1, wherein:

ratios between Pt and Rh of said respective cermet electrode layers ranges from 10:90 to 90:10 by weight ratio.

3. A NOx concentration-measuring apparatus comprising:

a first oxygen pump means for introducing a measurement gas from the outside of said apparatus into a first hollow space to adjust a partial pressure of oxygen in said measurement gas; and a second oxygen pump means for pumping out oxygen contained in said measurement gas from said measurement gas having said partial pressure of oxygen controlled by said first oxygen pump means and controlling said partial pressure of oxygen to have a predetermined value at which a NOx component is reduced or decomposed to pump out oxygen produced when said NOx component contained in an atmosphere in a second hollow space is reduced or decomposed, wherein:

a concentration of NOx in said measurement gas is detected by measuring a pumping current due to a pumping action of said second oxygen pump means of said NOx concentration-measuring apparatus;

a NOx-decomposing electrode of said second oxygen pump means for reducing or decomposing said NOx component comprises a plurality of cermet electrode layers each of which comprises an alloy of Pt—Rh and a ceramic component, a first of said cermet electrode layers being firmed on a ceramic substrate, and a second of said cermet electrode layers being formed on said first cermet electrode layer, wherein said respective cermet electrode layers have different ratios between said alloy of Pt—Rh and said ceramic component, said ratio between said alloy of Pt—Rh and said ceramic component in said first cermet electrode layer ranging from 20:80 to 50:50 by volume ratio, and said ratio between said alloy of Pt—Rh and said ceramic component in said second cermet electrode layer raging from 60:40 to 50:50 by volume ratio, and wherein proportions of said alloy of Pt—Rh in said respective cermet electrode layers are established such that said proportion is minimum in said first cermet electrode layer, which is a lowermost layer of said electrode, and maximum in said second cermet electrode layer, which is an uppermost layer of said electrode.

* * * * *

UNITED STATES PATENT AND TRADEMARK OFFICE
CERTIFICATE OF CORRECTION

| | | |
|---|---|---|
| PATENT NO. | : 7,156,966 B2 | Page 1 of 1 |
| APPLICATION NO. | : 10/419391 | |
| DATED | : January 2, 2007 | |
| INVENTOR(S) | : Kunihiko Nakagaki et al. | |

It is certified that error appears in the above-identified patent and that said Letters Patent is hereby corrected as shown below:

Column 11
    *Line 56*: please delete the first occurence of "to"

Column 12
    *Line 42*: please change "firmed" to --formed--

Signed and Sealed this

Twenty-seventh Day of March, 2007

JON W. DUDAS
*Director of the United States Patent and Trademark Office*